United States Patent [19]

Ergas

[11] Patent Number: 5,423,329
[45] Date of Patent: Jun. 13, 1995

[54] METHOD OF TREATMENT FOR URINARY INCONTINENCE

[75] Inventor: Martin Ergas, Coconut Grove, Fla.

[73] Assignee: Rehab Centers of America, Inc., Miami, Fla.

[21] Appl. No.: 228,580

[22] Filed: Apr. 15, 1994

[51] Int. Cl.⁶ ............................................. A61N 1/00
[52] U.S. Cl. ...................... 128/733; 607/138
[58] Field of Search ............ 128/733, 405, 734, 774, 128/778, 782; 607/138

[56] References Cited

U.S. PATENT DOCUMENTS

| | | |
|---|---|---|
| 3,628,538 | 12/1971 | Vincent . |
| 3,800,800 | 4/1974 | Garbe et al. ............ 607/138 X |
| 4,213,466 | 7/1980 | Stulen ...................... 128/733 |
| 4,396,019 | 8/1983 | Perry, Jr. ................ 128/733 |
| 4,580,578 | 4/1986 | Barsom .................... 607/138 |
| 4,632,126 | 12/1986 | Aguilar . |
| 4,790,328 | 12/1988 | Young ................... 128/733 X |
| 5,103,835 | 4/1992 | Yamada et al. . |
| 5,154,177 | 10/1992 | Eisman et al. .......... 128/733 X |
| 5,199,443 | 4/1993 | Maurer et al. .......... 607/138 |
| 5,277,197 | 1/1994 | Church et al. . |
| 5,291,902 | 3/1994 | Carman .................. 607/138 |

OTHER PUBLICATIONS

Burgio, Staying Dry, A Practical Guide to Bladder Control; pp. 133-137, Johns Hopkins Univ. Press.
Abrams, The Merck Manual of Geriatrics; pp. 92-105, Merck Sharp & Dohme Research Labs, 1990.
neuroEducator II, Operator's Manual, pp. 3-13, 1991.

*Primary Examiner*—Sam Rimell
*Attorney, Agent, or Firm*—Lott & Friedland

[57] ABSTRACT

A non-invasive method of treatment for urinary incontinence wherein the electromyographic biofeedback equipment is used on a patient by medical personnel without the necessity of insertion and removal of the catheter or neuromuscular stimulation, wherein the biofeedback results are monitored by both the medical personnel and the patient and are computed in "real-time" allowing contemporaneous instructions to the patient. The method includes the steps of preparing a patient for the method of treatment; attaching sensors of an electromyographic biofeedback device to the patient; monitoring biofeedback signals resulting from voluntary muscle contractions by the patient; interpreting the biofeedback signals; instructing the patient to control muscle contractions according to the signals; and developing a self-treatment program of muscle contraction maneuvers for the patient.

17 Claims, 4 Drawing Sheets

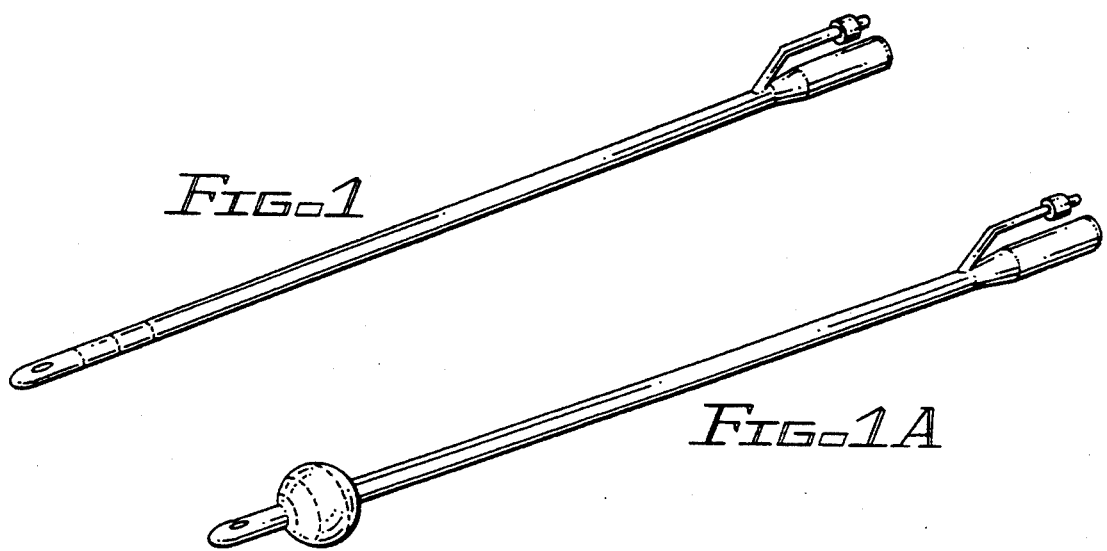
FIG.1
FIG.1A
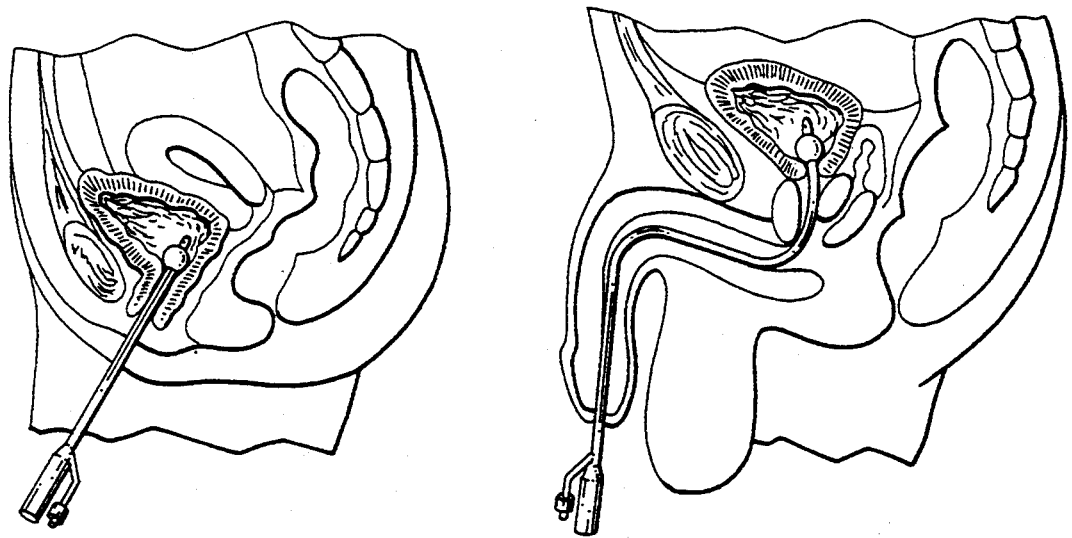
FIG.2
FIG.3
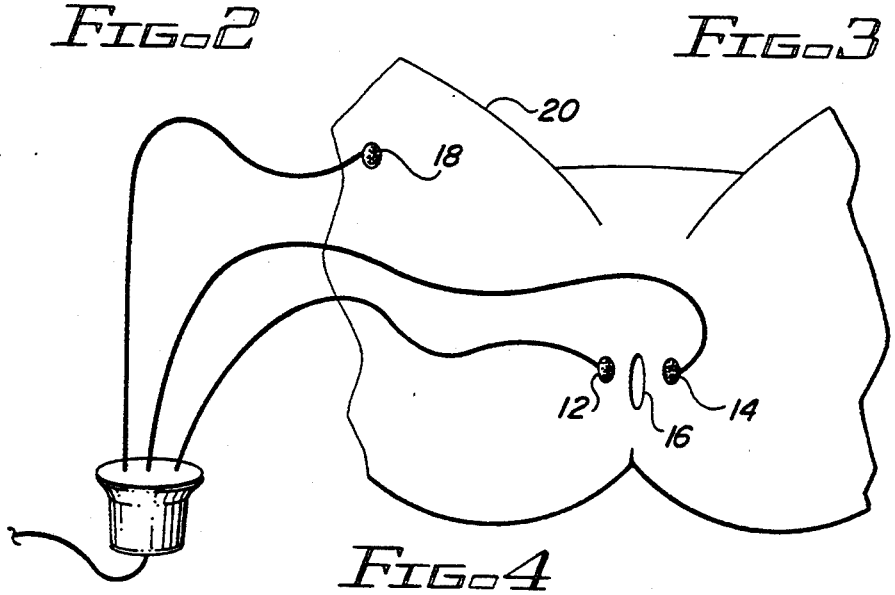
FIG.4

METHOD OF TREATMENT FOR URINARY INCONTINENCE

TECHNICAL FIELD

This invention relates generally to a method of treatment for urinary incontinence, and this invention specifically relates to a method of treatment for urinary incontinence which alters bladder dysfunction by teaching patients to change physiologic responses which mediate bladder control with the aid of electromyographic biofeedback (EMG-BF), allowing patients to return to more productive lifestyles and a better quality of life.

BACKGROUND OF THE INVENTION

At least 10 million Americans suffer from urinary incontinence. The U.S. Department of Health and Human Services *Clinical Practice Guideline: Urinary Incontinence in Adults* has estimated that the annual cost of treatment exceeds $10 billion.

The most common forms of urinary incontinence are stress incontinence, urge incontinence and overflow incontinence. Stress incontinence is the most common type and is the result of pressure on the bladder during exercise, coughing, laughing or other body movements. Urge incontinence is the involuntary loss of urine due to an abrupt and urgent need to urinate. Overflow incontinence is leakage of small amounts of urine from a bladder that is always full.

The United States Department of Health and Human Service Clinical Practice Guideline divides the treatment of urinary incontinence into three major categories: pharmacologic; surgical; and behavioral.

An example of pharmacologic treatment is illustrated in U.S. Pat. No. 5,192,751 to Thor, incorporated herein by reference. Thor describes a method of treating urinary incontinence in a mammal which comprises administering an effective amount of a competitive NMDA antagonist.

The disadvantage of pharmacologic treatment such as that described in Thor is the possible side effects caused by the drugs used. Pharmacologic treatment is also inappropriate for long-term maintenance use and is not curative. Pharmacologic therapy for urge incontinence is designed to inhibit uncontrolled detrusor contractions. Drugs are usually effective in 80 to 85% of patients with uninhibited bladder contractions and symptoms of urinary frequency, urgency and incontinence. Anticholinergic medications are the mainstay of this type of treatment and the side effects common to this group of drugs include dry mouth, blurring of vision, constipation and drowsiness. For stress incontinence, the pharmacologic therapy is directed to the stimulation of certain receptors and muscles, including the internal sphincter. Drugs usually have only a 75% effective rate for patients with stress incontinence of a mild to moderate degree. Side effects from the drugs usually prescribed to treat stress incontinence can be severe and include headache, elevated blood pressure, nervousness, tachycardia and arrhythmia.

An example of surgical treatment is illustrated in U.S. Pat. No. 5,123,428 to Schwarz, incorporated herein by reference. Schwarz describes a method for implanting an artificial sphincter to control urinary incontinence in a patient including two implantation procedures and an intervening interval of testing and healing.

Surgical procedures are available for the treatment of certain physiological causes of incontinence. The major disadvantage of surgical treatment for urinary incontinence such as that described in Schwarz is the increased chance of infection and the risk of other complications as with any invasive surgical procedure. Another significant disadvantage of surgical treatment is that it is the most expensive method of treatment and, even though the procedure may not be successful in attaining continence, the effect may be irreversible.

Of the three treatment categories, behavioral treatment is the least invasive and least dangerous procedure for the patient. The objective of behavioral treatment is to reduce the chance of triggering an uninhibited detrusor muscle contraction or an incomplete closure of the sphincter muscle by regulating the frequency of voiding and preventing the bladder from being overstretched. Behavioral treatment has proven effective for patients suffering from urge, stress and mixed incontinence. However, patients with overflow incontinence are not primary candidates for behavioral intervention.

Various muscles control urination. Behavioral treatment for urinary incontinence focuses on the development of appropriate muscle contraction maneuvers involving certain of these muscles. Such treatment has been effective in controlling urinary incontinence and also is a non-invasive method with no side effects.

The detrusor and the internal and external sphincter muscles are the three structures responsible for storage and evacuation of urine from the bladder. Contraction of the internal sphincter prevents leakage of urine from the bladder. Dysfunction of one or more of these muscles is often the cause of incontinence.

Biofeedback is a behavioral training technique that is used to correct a host of physiological and psychological conditions. In the treatment of urinary incontinence, biofeedback measures a person's bodily response, amplifies that measurement, and provides visual and/or auditory feedback to the patient that allows the patient to observe the effect of appropriate muscular contraction maneuvers on the bladder.

It is possible to develop appropriate muscle contraction maneuvers without biofeedback. However, more than 80 percent of the patients treated for urge, stress or mixed incontinence are improved or completely continent after behavioral training with biofeedback. Furthermore, without biofeedback, it is possible that the patient will contract inappropriate muscles during treatment and, as a result, the patient may aggravate the incontinent condition. Thus, biofeedback is an important tool in restoring the proper function to a noncompliant bladder.

The use of biofeedback in connection with incontinence treatment usually involves inserting a catheter (FIGS. 1-3) or other sensory device into the bladder. With this procedure, as the bladder fills with water, the patient is able to use the biofeedback equipment to watch the recording of the increasing pressure in the bladder. The patient may experience some discomfort from the insertion or removal of the catheter or other sensory device and there is a 1 to 2 percent risk of infection from the catheterization.

Another technique using biofeedback in connection with incontinence treatment is described in U.S. Pat. No. 5,291,902 to Carman. The technique in Carman includes allowing the patient to use a portable electromyographic measuring unit which outputs a signal when the measurement is above a pre-set threshold value. A major disadvantage of this technique is that patients cannot receive contemporaneous instructions from medical personnel regarding their muscle contractions. A further disadvantage is that since patients only obtain a signal if the pre-set threshold is reached, levels of incremental improvement cannot be monitored, nor can any level of decline in muscle contractions be measured. Finally, since the measuring unit described in Carman uses only two electrodes, the sensitivity necessary to obtain meaningful information about the patient's activity can not be achieved.

A further technique described in Carman is neuromuscular stimulation. This technique is given in the form of repeated applications of electrical pulses to the appropriate pelvic floor muscles to cause them to repeatedly contract and relax. Such stimulation causes muscle growth and increased muscle strength. However, there are many drawbacks to the use of neuromuscular stimulation. One drawback with neuromuscular stimulation is that repeated intensive sessions are required in order for the technique to be effective. Another drawback is that the activity may overwork the muscles and result in debilitation, rather than strengthening. In addition, the electric pulses also may be painful to the patient. Finally, in order to attain sufficient stimulation to the pelvic floor muscles, the electrodes must be applied intrarectally or intravaginally. Thus, the technique may be considered invasive to the patient.

Thus, there are several problems with the current methods of treatment for urinary incontinence, such as (i) the drugs used in pharmacologic treatment may have side effects, (ii) surgical treatment is invasive, has risks of complications, and is painful, (iii) behavioral treatment without biofeedback may reinforce inappropriate muscle contractions, (iv) behavioral treatment with portable biofeedback equipment does not allow the patient to receive contemporaneous instructions from a physician or nurse, and (v) neuromuscular stimulation is invasive, may be painful and may cause inappropriate muscle activity.

One possible solution to these problems is to provide a method of treatment which does not utilize drugs with harmful or uncomfortable side effects, and that does not utilize surgical methods which can lead to infection.

Another possible solution to these problems is to provide a behavioral method of treatment wherein the EMG-BF equipment is used on the patient by medical personnel in behavioral training without the necessity of insertion and removal of the catheter.

Another possible solution to these problems is to provide a behavioral method of treatment wherein the patient, in addition to the medical personnel, may visually monitor the EMG-BF results.

Another possible solution to these problems is to provide a behavioral method of treatment in which the EMG-BF results are computed in "real-time" so that medical personnel can give contemporaneous instructions to the patient.

Another possible solution to these problems is to allow development of the appropriate muscle contraction maneuvers without neuromuscular stimulation.

Another possible solution to these problems is to provide a behavioral method of treatment which is less invasive than normal procedures and results in no patient discomfort and no risk of infection or other side effects.

Thus, there has been a need in the art for a less invasive behavioral method of treatment of urinary incontinence wherein EMG-BF equipment is used on the patient by medical personnel without the necessity of insertion and removal of the catheter and the biofeedback results are visually monitored by the medical personnel and the patient and are computed in "real-time" allowing contemporaneous instructions from the medical personnel and responses from the patient.

SUMMARY OF THE INVENTION

The present invention solves significant problems in the art by providing a behavioral method of treatment for urinary incontinence wherein electromyographic biofeedback equipment is used on the patient by medical personnel without the necessity of insertion and removal of a catheter and the electromyographic biofeedback results are monitored by the medical personnel and the patient and are computed in "real-time" allowing contemporaneous instructions from the medical personnel and responses from the patient.

Generally described, the present invention provides a behavioral method of treatment for urinary incontinence using biofeedback.

In a preferred embodiment of the invention, the method comprises a behavioral method for treating urinary incontinence in a patient by medical personnel, comprising preparing the patient for the method of treatment; attaching sensors of a biofeedback device to the patient; monitoring biofeedback signals resulting from voluntary muscle contractions by the patient; interpreting the biofeedback signals; instructing the patient to control muscle contractions according to the signals; and developing a self-treatment program for the patient.

The behavioral method further comprises providing a patient monitor for the patient's monitoring of biofeedback signals resulting from voluntary muscle contractions by the patient. The biofeedback device is an electromyographic biofeedback device.

The step of preparing the patient for the method of treatment comprises examining the patient urologically; and instructing the patient to record daily fluid intake and bladder voiding.

The step of attaching the sensors comprises attaching two sensors to either side of the patient's anus; attaching one sensor under the patient's thigh; attaching two sensors across the patient's lower abdomen; and attaching one sensor on the patient's upper thigh.

The step of monitoring biofeedback signals comprises visually observing the signals on at least one monitor, recording the signals electronically, and printing the signals.

The step of interpreting the biofeedback signals comprises viewing a baseline measurement, a peak measurement, a sustained measurement, and a duration measurement for the patient's pelvic muscle; comparing the measurements to a set of pre-determined measurements; and communicating an interpretation of the measurements.

The step of instructing the patient to control muscle contractions according to the signals comprises instructing the patient to control muscle contractions of the patient's pelvic muscle according to the signals; and instructing the patient to control muscle contractions of the patient's abdominal muscle according to the signals.

In a preferred embodiment, the step of instructing the patient to control muscle contractions of the patient's pelvic muscle comprises instructing the patient to relax the patient's pelvic muscle.

In an alternate embodiment, the step of instructing the patient to control muscle contractions of the patient's pelvic muscle comprises instructing the patient to contract the patient's pelvic muscle.

In a preferred embodiment, the step of instructing the patient to control muscle contractions of the patient's abdominal muscle comprises instructing the patient to relax the patient's abdominal muscle.

In an alternate embodiment, the step of instructing the patient to control muscle contractions of the patient's abdominal muscle comprises instructing the patient to contract the patient's abdominal muscle.

In a preferred embodiment, the self-treatment program comprises muscle contraction maneuvers of the patient's muscles.

In an alternate embodiment, the self-treatment program comprises bladder training for the patient, habit training for the patient, or prompted voiding by the patient.

Accordingly, it is an object of the present invention to provide a behavioral method of treatment for urinary incontinence in a patient by medical personnel using non-invasive electromyographic biofeedback.

It is another object of the present invention to provide a behavioral method comprising preparing a patient for the method of treatment; attaching sensors of an electromyographic biofeedback device to the outside body of the patient; monitoring biofeedback signals resulting from voluntary muscle contractions by patient; interpreting the biofeedback signals; instructing the patient to control muscle contractions according to the signals; and developing a self-treatment program for the patient.

Accordingly, it is a feature of the invention for both the patient and the medical personnel to be able to monitor visually the signals on at least one monitor and/or record the signals electronically; and print the signals.

An advantage of the invention is that the method of treatment does not utilize drugs with harmful or uncomfortable side effects, and does not utilize surgical methods which can lead to infection, and does not use neuromuscular stimulation.

Another advantage of the invention is that the biofeedback equipment is used on the patient by medical personnel in behavioral training without the necessity of insertion and removal of a catheter.

Another advantage of the invention is that the biofeedback results are computed in "real-time" allowing medical personnel to contemporaneously instruct the patient of the appropriate muscle contractions.

Another advantage of the invention is that the method of treatment is less invasive than normal procedures (i.e. the invention is completely non-invasive) and results in no patient discomfort and no risk of infection or other side effects.

Another advantage is that since the treatments are monitored by medical personnel, the patient will receive contemporaneous instructions and reinforcement during treatment from the medical personnel, daily contact and monitoring during the treatment period, and regular follow-up and monitoring after discharge.

These and other objects, features, and advantages of the present invention may be more clearly understood and appreciated from a review of the following detailed description of the disclosed embodiments and by reference to the appended drawings and claims.

BRIEF DESCRIPTION OF THE DRAWING FIGURES

FIG. 1 is a plan view showing a catheter commonly used in the industry for treating urinary incontinence having an inflatable balloon tip which holds the catheter inside the bladder.

FIG. 2 is a cross-sectional view of an inflated urinary catheter positioned inside the bladder of a female.

FIG. 3 is a cross-sectional view of an inflated urinary catheter positioned inside the bladder of a male.

FIG. 4 is a perspective view of the biofeedback system attached to the patient in a preferred method of the invention.

DETAILED DESCRIPTION OF THE PREFERRED EMBODIMENT

Figure 5:
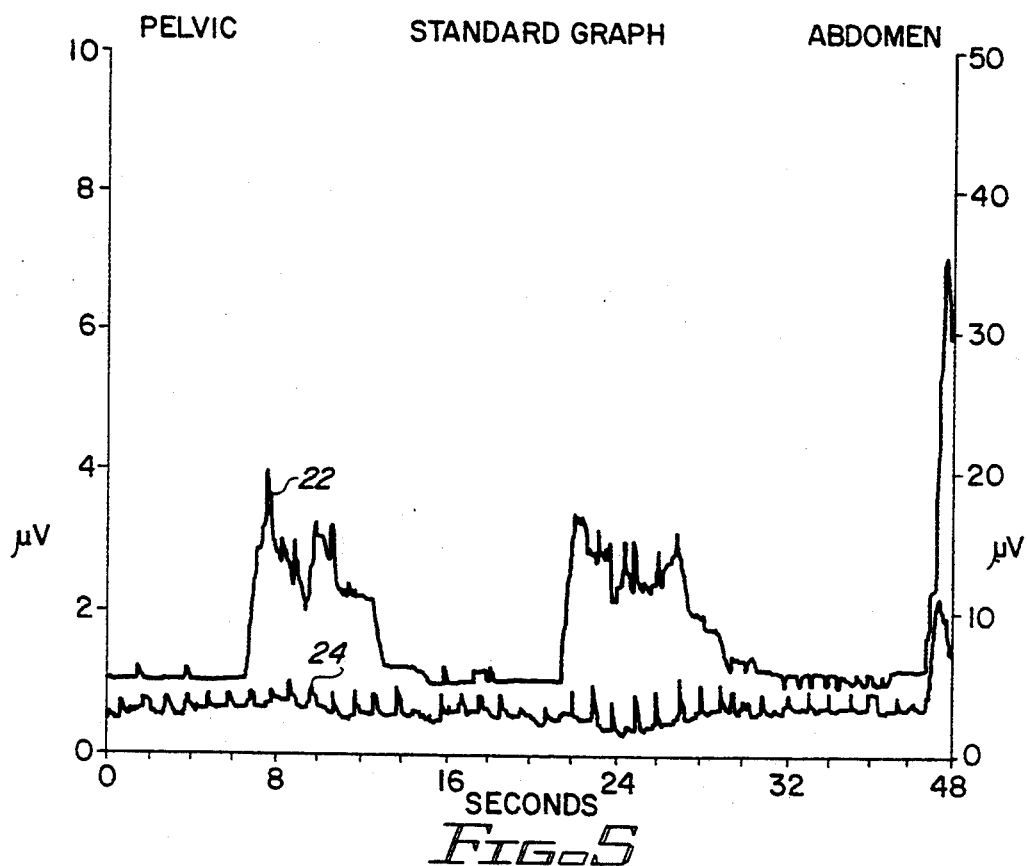
FIG. 5 is a graph illustrating the data report for a first test patient for session #2.

In the preferred method of this invention, a special electromyographic biofeedback (EMG-BF) system, known as the neuroEducator II EMG System, is used. The application of the biofeedback system is non-invasive and does not require catheterization. Thus, there is no patient discomfort and no risk of infection or other side effects.

Generally, the method of treatment for urinary incontinence of the present invention is based upon behavioral treatment techniques without neuromuscular stimulation, including bladder training, habit training, prompted voiding, and muscle contraction maneuvers. In addition, the method couples the patient's development of appropriate muscle contractions with EMG-BF, which uses computer display instruments to relay information to medical personnel and patients about the patient's physiologic activity. The EMG-BF allows levels of incremental improvement to be monitored or any level of decline in muscle contractions. The EMG-BF assists medical personnel in the evaluation of the patients' progress, prevents the patient from contracting inappropriate muscles, and reinforces the patient's appropriate muscle contraction maneuvers.

The preferred method emphasizes appropriate contraction and relaxation of these muscles to increase muscle tone and resistance in the urethral passage. Initially, medical personnel work with the patient in identifying and locating the appropriate muscles that need corrective treatment. Later in the treatment program, the patient maneuvers the appropriate muscles in sessions supervised by a registered nurse and monitored by a physician for the purpose of restoring the proper functioning of the bladder. Upon the completion of the medically supervised treatments, the patient continues the muscle contraction maneuvers on a daily basis in order to maintain the previously achieved muscle control.

The present invention is directed to a method for the treatment of urinary incontinence which is based upon behavioral treatment techniques, particularly development of appropriate muscle contractions, and which utilizes EMG-BF as an evaluation, education, and reinforcement tool. The method consists of patient diagnosis and evaluation; education of the patient regarding behavioral treatment techniques; regular and consistent record keeping as to fluid intake, bladder voiding and completion of self-treatment program techniques, including muscle contraction maneuvers; 6 to 12 behavioral treatment sessions, including muscle contraction maneuvers coupled with EMG-BF, supervised by a registered nurse and monitored by a urologist or other physician; daily monitoring of patient status by a registered nurse during the medically supervised treatment phase; continued daily self-treatment program techniques, including muscle contraction maneuvers, following completion of the medically supervised treatment sessions to reinforce the appropriate behavioral activity and to maintain the previously achieved muscle control; and post-discharge patient monitoring at two-month intervals.

While behavioral methods for the treatment of urinary incontinence may be applied in various forms, the preferred method of the present invention uses a seven-step protocol to maximize the results from the treatment. The seven steps are as follows:

1. All patients are required to have been examined and evaluated by a urologist, to have had a urological work-up and medical history prepared, and to have a prescription from a urologist or other physician to the treatment program.
2. For three days prior to the first office treatment session, and during the period of office treatment sessions, all patients are required to keep a precise daily fluid intake and bladder voiding diary.
3. All patients are evaluated for muscle control by a registered nurse utilizing the biofeedback system for EMG-BF. The EMG-BF system provides real time biofeedback and continuous sampling by special analog integrator hardware read by a microprocessor at a 100 HZ rate. With this method, there are two biofeedback computer screens to allow the patient and registered nurse or physician to view the patient's activity at the same time. Patients view the computer screen to see the correct muscle contractions, length of contractions, and muscle relaxation. Together;, the registered nurse and the patient's physician determine if a patient is an acceptable candidate for the treatment program based on the patient's likelihood of having a reduction in incontinence from the treatment.
4. Office treatment sessions are conducted by a registered nurse for a patient once or twice a week. Ideally, a patient will have a minimum of 6 and a maximum of 12 treatment sessions. During the initial sessions, the registered nurse develops appropriate muscle contraction maneuver criteria for the patient. The patient maneuvers the appropriate muscles during the sessions while under the supervision of the registered nurse without neuromuscular stimulation. The registered nurse provides the patient's urologist or other physician with a progress report following each treatment session.
5. The registered nurse develops a daily self-treatment program for the patient. The self-treatment program consists of muscle contraction maneuvers and other appropriate behavioral techniques such as bladder training, habit training and prompted voiding. The registered nurse provides instructions to the patient with regard to these treatment techniques.
6. On the days between medically supervised treatment sessions, the registered nurse contacts the patient or the patient's caregiver to verify that the patient has completed and recorded his self-treatment program for that day.
7. After the patient's discharge, the daily muscle contraction maneuvers and other behavioral techniques are continued by the patient. The registered nurse will continue to monitor the patient's progress after his discharge at intervals of 2 months.

The registered nurse's activity is conducted under the supervision of a physician. The role of the registered nurse in the treatment program is to evaluate the patient for likelihood of improvement in continence from the treatment program; educate the patient as to the nature and goals of the treatment program; develop the muscle contraction maneuver criteria which is appropriate for the patient; provide supervision of the treatment and positive reinforcement of the patient's effort and progress; train the patient to read and understand the EMG-BF computer screens; develop a self-treatment program for the patient; chart the patient's progress and provide progress reports to the patient's physician; and monitor the patient's progress during and after treatment. The registered nurses who utilize the method will receive on a regular basis information as to new developments in the treatment of urinary incontinence and reinforcement of the proper utilization of the method to insure quality control.

The invention emphasizes the least invasive and least dangerous method of treatment for urinary incontinence. The method of treatment has no reported side effects and does not in any way limit the use of other methods of treatment in the future and does not require neuromuscular stimulation.

The method requires a commitment by the patient to regular and continued maintenance of the treatment program developed for the patient. Most patients who are willing to make the commitment show improvement ranging from complete dryness to reduced wetness.

The preferred biofeedback system consists of an IBM compatible computer, operator monitor, patient color monitor, color printer, analog integrator, and 100 HZ EMG processor: with patient sensor cables. While in use, the biofeedback system provides the patient with real time biofeedback and continuous sampling of muscle activity. The preferred system was specifically designed for assistance in treatment of urinary and fecal incontinence, nocturia, constipation and post-prostate surgery rehabilitation. Four sensors are used for more sensitivity in the signal readings. The method of treatment must be administered by medical personnel, since the patient would be unable to properly hook himself up to this equipment.

Turning now to FIG. 4, to utilize the biofeedback system 10, sensors are placed at specific sites on the patient to monitor the elicited EMG. The four cable ends are numbered to correspond with the channels available to monitor EMG feedback. One to four channels can be used in any combination for the treatment. Each muscle to be monitored will require three electrode sensor wires with snap connectors on one end and pin connectors on the other end, two green and one black. The green pins and snap connectors are active and the black pins and snap connectors are the reference. In a preferred method, two active or green electrodes, 12, 14 are placed parallel on either side and as close as possible to the anus 16. One ground or black electrode 18 is placed under the thigh 20 on the right or left side. Two active or green electrodes are placed parallel across the lower abdomen just above the pubic hair line to the right or left of midline. Finally, a ground or black electrode is placed on the right or upper thigh.

The patient is asked to contract for as long and as strong as he can. As the patient contracts and relaxes the appropriate muscles, the patient's bodily responses are transmitted through the cables to the EMG processor. No neuromuscular stimulation is used. Through specially designed urinary incontinence treatment program software, the processor records the information and through the monitors allows the patient and operator to observe the measurement of muscle contractions during the patient's treatment. The signals are displayed in "real time", contemporaneously with the muscle activity. Typical data reports are illustrated in FIGS. 5-10. The EMG activity that is presented on the graph is measured in microvolts RMS. As activity is detected, it will be measured and displayed based on a sensitivity scale that has been pre-selected by the operator. A change in measurements would represent a level of incremental improvement or decline in muscle contractions. The measurements are monitored graphically by viewing a baseline measurement, a peak measurement, a sustained measurement, and a duration measurement for the patient's muscle activity. As shown in FIGS. 5-10, the measurements are represented graphically in voltage over time.

FIG. 5 illustrates the data report of a patient complaining of leaking and frequency during session #2 with a goal to increase pelvic muscle contraction (PMC) and duration to decrease frequency and leaking. The report for the pelvic muscle 22 shows weak muscle contraction and only a fair duration. The report for the abdominal muscle 24 shows proper relaxation of the abdominal muscle with contraction of pelvis muscle. At the time of session #2, the patient showed increase in pelvic muscle contraction (PMC) and duration and was instructed to continue exercises.

Figure 6:
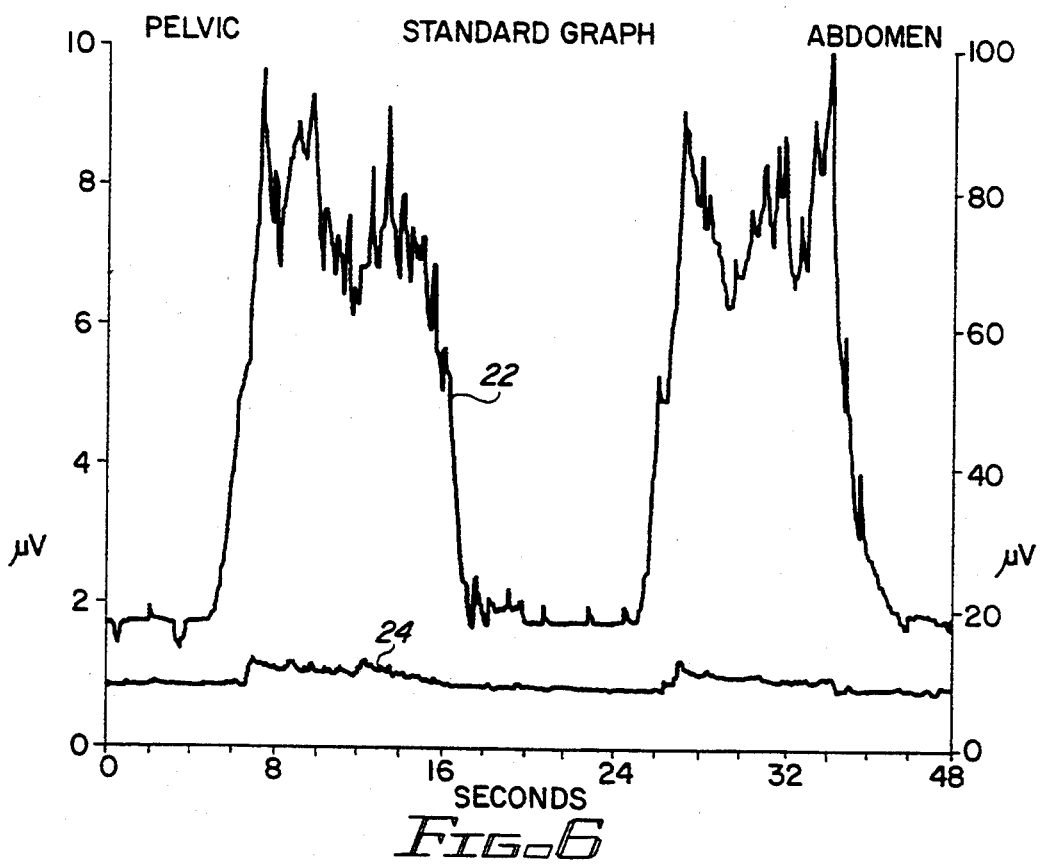
FIG. 6 is a graph illustrating the data report for a first test patient for session #5.

FIG. 6 illustrates the data report of the same patient in FIG. 5 during session #5. The report for the pelvic muscle 22 shows fair muscle contraction and good duration. The report for the abdominal muscle 24 some slight recruitment of abdominal muscle duration pelvic muscle contraction.

Figure 7:
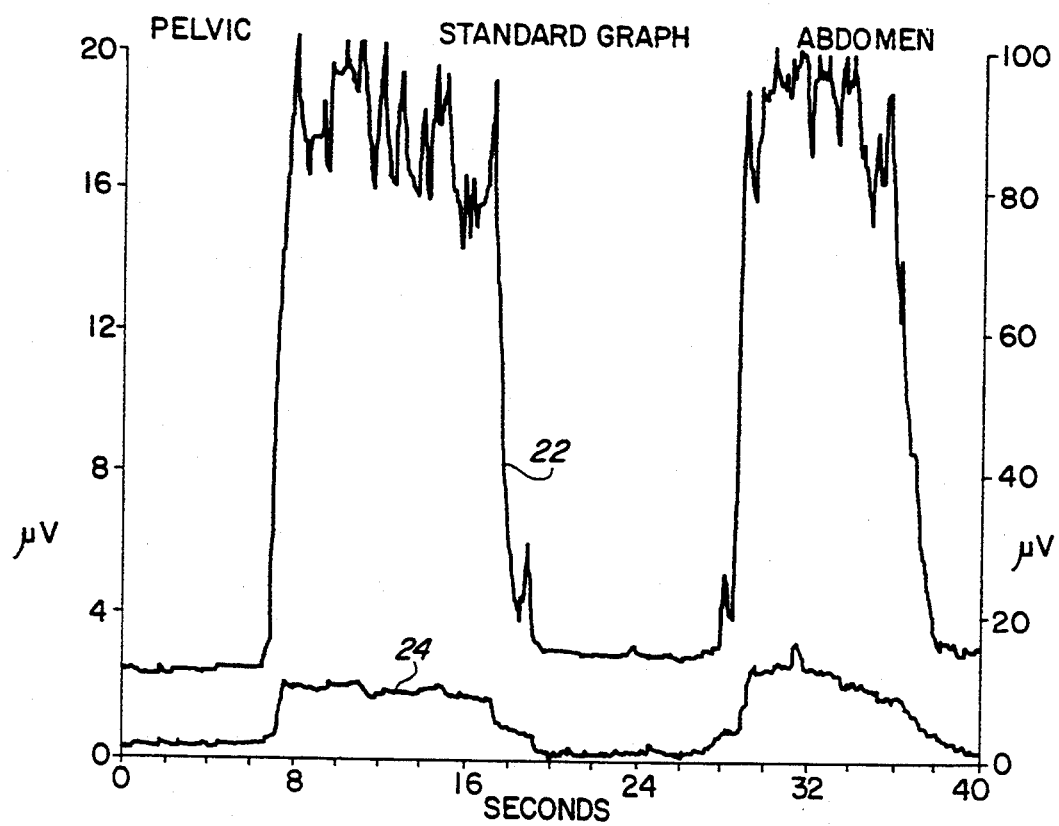
FIG. 7 is a graph illustrating the data report for a first test patient for session #8.

FIG. 7 illustrates the data report for the same patient in FIG. 5 during session #8. The report for the pelvic muscle 22 shows good muscle contraction and good duration. The report for the abdominal muscle 24 shows recruiting abdominal muscles with each pelvic muscle contraction. Increased PMC and maximum sustained PMC was noted. The patient's diary showed dryness and the patient was very pleased with the progress and was discharged from the program at that time with instructions to continue exercises.

Figure 8:
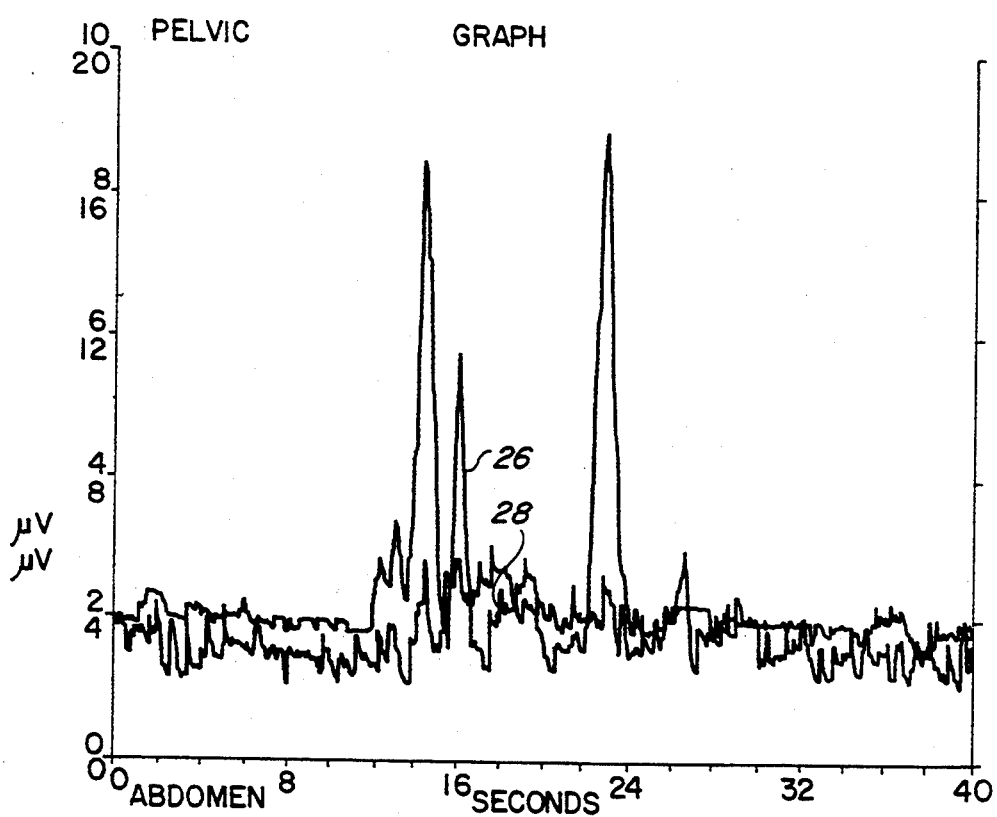
FIG. 8 is a graph illustrating the data report for a second test patient for session #2.
Figure 9:
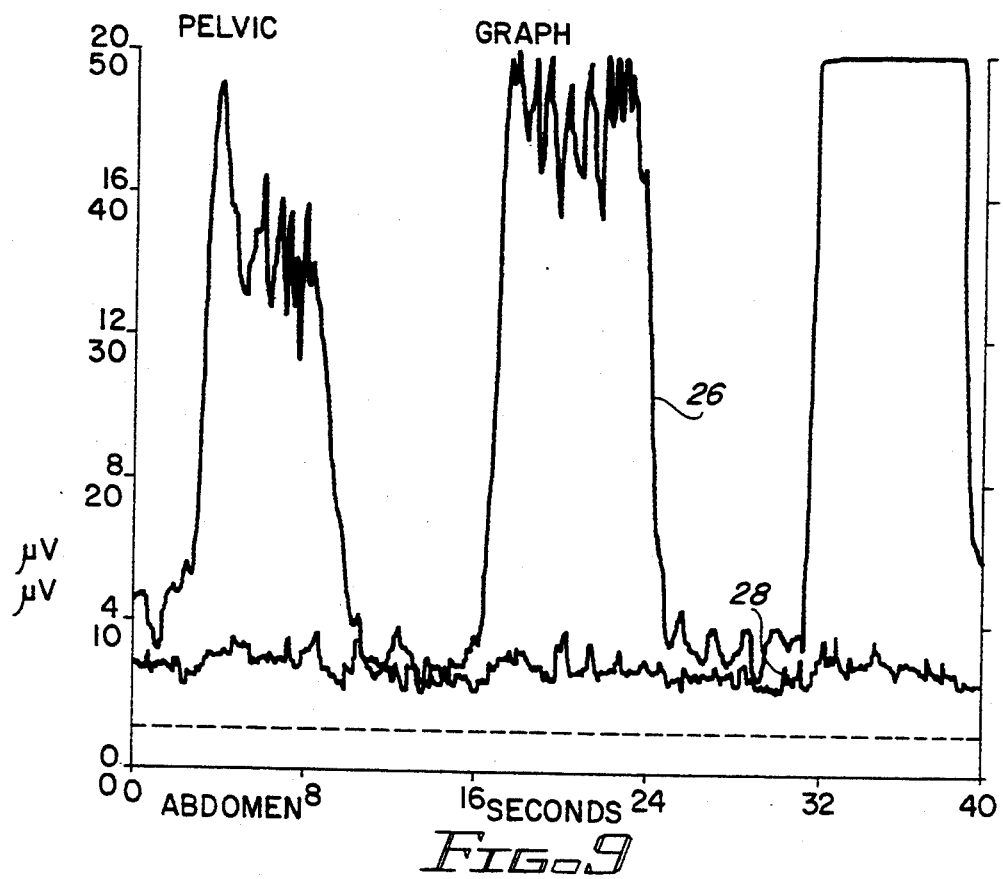
FIG. 9 is a graph illustrating the data report for a second test patient for session #3.
Figure 10:
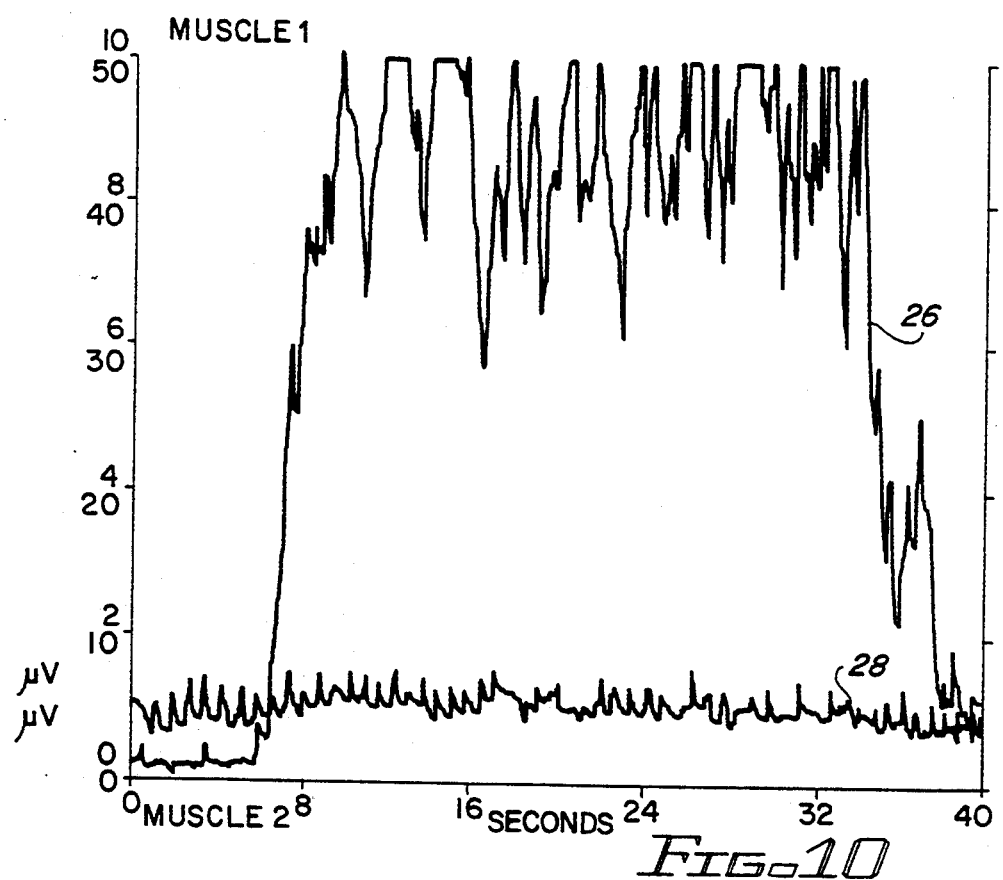
FIG. 10 is a graph illustrating the data report for a second test patient for session #10.

FIGS. 8-10 show the data reports for a second patient whose chief complaint was stress and urge incontinence. FIG. 8 shows the report for session #2. The report for the pelvic muscle 26 shows weak muscle contraction and poor duration. The report for the abdominal muscle 28 shows some recruitment of abdominal muscle with pelvic muscle contraction.

FIG. 9 shows the report for session #3. The report for the pelvic muscle 26 shows good muscle contraction and fair duration. The report for the abdominal muscle 28 no recruitment of abdominal muscle with pelvic muscle contraction.

FIG. 10 shows the report for session #10. The report for the pelvic muscle 26 shows good muscle contraction and very good duration. The report for the abdominal muscle 28 shows no recruitment of the abdominal muscle with pelvic muscle contraction. At the time of session #10 the patient was no longer wearing pads all the time with only two damp episodes in one week. The patient was to continue exercises.

A sample of 156 patient charts for patients who completed the treatment program and had at least three office treatment sessions was analyzed as of Dec. 30, 1993. Of the sample, 51 patients (33%) were completely dry and symptom free, 38 patients (24%) were 90% continent and 90% symptom free, and 49 patients (31%) had 25% to 89% improvement. Only 18 patients (12%) showed no improvement. Therefore, 88% of the patients in the sample showed substantial (at least 25%) improvement and 57% of those patients showed at least 90% improvement.

Accordingly, it will be understood that the preferred embodiment and alternative embodiment of the present invention have been disclosed by way of example and that other modifications and alterations may occur to those skilled in the art without departing from the scope and spirit of the appended claims.

What is claimed is:

1. A behavioral method for treating urinary incontinence in a patient by medical personnel, comprising:
    attaching two sensors of a biofeedback device to either side of said patient's anus;
    attaching one sensor of a biofeedback device under said patient's thigh;
    attaching two sensors of a biofeedback device across said patient's lower abdomen;
    attaching one sensor of a biofeedback device on said patient's upper thigh;
    monitoring biofeedback signals graphically which result from voluntary muscle contractions by said patient; and
    instructing said patient to control muscle contractions according to said signals.

2. The behavioral method of claim 1 further comprising, providing a patient monitor for said patient's monitoring of biofeedback signals resulting from voluntary muscle contractions by said patient.

3. The behavioral method of claim 1 wherein said biofeedback device is a electromyographic biofeedback device.

4. The behavioral method of claim 1 further comprising the step of preparing said patient for said method of treatment comprising:
    examining said patient urologically; and
    instructing said patient to record daily fluid intake and bladder voiding.

5. The behavioral method of claim 1 wherein said step of monitoring biofeedback signals comprises:
    visually observing said signals on at least one monitor, whereby a change in measurements represents levels of incremental improvement or decline in muscle contractions, said measurements are monitored graphically by viewing a baseline measurement, a peak measurement, a sustained measurement, and a duration measurement for said patient's pelvic muscle, wherein said measurements are represented graphically in voltage over time.

6. The behavioral method of claim 5, further comprising:
recording said signals electronically; and
printing said signals.

7. The behavioral method of claim 1 wherein said step of instructing said patient to control muscle contractions according to said signals comprises:
instructing said patient to control muscle contractions of said patient's pelvic muscle according to said signals; and
instructing said patient to control muscle contractions of said patient's abdominal muscle according to said signals.

8. The behavioral method of claim 7 wherein said step of instructing said patient to control muscle contractions of said patient's pelvic muscle comprises instructing said patient to relax said patient's pelvic muscle.

9. The behavioral method of claim 7 wherein said step of instructing said patient to control muscle contractions of said patient's pelvic muscle comprises instructing said patient to contract said patient's pelvic muscle.

10. The behavioral method of claim 7 wherein said step of instructing said patient to control muscle contractions of said patient's abdominal muscle comprises instructing said patient to relax said patient's abdominal muscle.

11. The behavioral method of claim 7 wherein said step of instructing said patient to control muscle contractions of said patient's abdominal muscle comprises instructing said patient to contract said patient's abdominal muscle.

12. The behavioral method of claim 1 further comprising the step of developing of a self-treatment program comprising muscle contraction maneuvers of said patient's muscles.

13. The behavioral method of claim 1 further comprising the step of developing of a self-treatment program comprising bladder training for said patient.

14. The behavioral method of claim 1 further comprising the step of developing of a self-treatment program comprising habit training for said patient.

15. The behavioral method of claim 1 further comprising the step of developing of a self-treatment program comprising prompted voiding by said patient.

16. A behavioral method for treating urinary incontinence in a patient by medical personnel, comprising:
attaching sensors of an electromyographic biofeedback device to said patient, wherein said sensors are attached by attaching two sensors to either side of said patient's anus; attaching one sensor under said patient's thigh; attaching two sensors across said patient's lower abdomen; and attaching one sensor on said patient's upper thigh;
monitoring biofeedback signals resulting from voluntary muscle contractions by patient by visually observing said signals on at least one monitor, whereby a change in measurements represents levels of incremental improvement or decline in muscle contractions, said measurements are monitored graphically by viewing a baseline measurement, a peak measurement, a sustained measurement, and a duration measurement for said patient's pelvic muscle, wherein said measurements are represented graphically in voltage over time; and
instructing said patient to control muscle contractions according to said signals.

17. A behavioral method for treating urinary incontinence in a patient by medical personnel, comprising:
preparing said patient for said method of treatment comprising the steps of examining said patient urologically and recording daily fluid intake and bladder voiding;
attaching sensors of an electromyographic biofeedback device to said patient, wherein said sensors are attached by attaching two sensors to either side of said patient's anus; attaching one sensor under said patient's thigh; attaching two sensors across said patient's lower abdomen; and attaching one sensor on said patient's upper thigh;
monitoring biofeedback signals graphically which result from voluntary muscle contractions by patient;
instructing said patient to control muscle contractions according to said signals comprising instructing said patient to control muscle contractions of said patient's pelvic muscle according to said signals and instructing said patient to control muscle contractions of said patient's abdominal muscle according to said signals; and
developing a self-treatment program for said patient wherein said self-treatment program comprises muscle contraction maneuvers.

* * * * *